United States Patent [19]

Kehoe

[11] Patent Number: 4,975,270

[45] Date of Patent: Dec. 4, 1990

[54] ELASTOMER ENCASED ACTIVE INGREDIENTS

[75] Inventor: Gary S. Kehoe, Briarcliff Manor, N.Y.

[73] Assignee: Nabisco Brands, Inc., East Hanover, N.J.

[21] Appl. No.: 40,970

[22] Filed: Apr. 21, 1987

[51] Int. Cl.$^5$ .......................... A61K 9/16; A61K 9/22; A61K 9/68

[52] U.S. Cl. .......................... 424/48; 424/43; 424/438; 424/439; 424/440; 424/441; 424/442; 424/490; 424/493; 131/352; 426/3; 426/801; 514/951; 514/965

[58] Field of Search .................. 424/48, 440, 441, 490, 424/493, 43, 438, 439, 442; 426/3, 801; 131/352

[56] References Cited

U.S. PATENT DOCUMENTS

| | | |
|---|---|---|
| 904,521 | 11/1908 | Ellis .......................... 426/3 |
| 2,987,445 | 6/1961 | Levesque .................. 424/469 |
| 3,071,476 | 1/1963 | Werft et al. ............... 426/5 |
| 3,091,567 | 5/1963 | Wurzburg .................. 424/418 |
| 3,166,078 | 1/1965 | Parmele et al. ........... 131/366 |
| 3,202,514 | 8/1965 | Burgess et al. ............ 426/532 |
| 3,297,452 | 1/1967 | Wing et al. ................ 426/6 |
| 3,312,594 | 4/1967 | Cyr et al. ................... 424/117 |
| 3,325,368 | 6/1967 | Wood ........................ 424/401 |
| 3,594,467 | 7/1971 | Christenson et al. ..... 424/465 |
| 3,806,350 | 4/1974 | Kuhn et al. ................ 106/162 |
| 3,901,248 | 8/1975 | Lichtneckert et al. .... 424/48 |
| 3,953,657 | 4/1976 | Yamaguchi et al. ....... 428/406 |
| 3,957,964 | 5/1976 | Grimm, III ................ 424/49 |
| 4,022,887 | 5/1977 | Harris et al. ............... 424/57 |
| 4,059,686 | 11/1977 | Hoya et al. ................ 424/435 |
| 4,066,754 | 1/1978 | Chou ......................... 514/157 |
| 4,087,557 | 5/1978 | Bakal et al. ................ 426/3 |
| 4,129,638 | 12/1978 | Ritze ......................... 524/47 |
| 4,230,687 | 10/1980 | Sair et al. .................. 424/485 |
| 4,250,163 | 2/1981 | Nagai et al. ............... 424/434 |
| 4,259,355 | 3/1981 | Marmo et al. ............. 426/5 |
| 4,260,635 | 4/1981 | Fisher ....................... 426/3 |
| 4,261,941 | 4/1981 | Sherman et al. .......... 264/117 |
| 4,309,374 | 1/1982 | Pollard ..................... 264/115 |
| 4,344,968 | 8/1982 | Aoda et al. ................ 424/81 |
| 4,384,004 | 5/1983 | Cea et al. .................. 426/3 |
| 4,386,106 | 5/1983 | Merritt et al. ............. 426/5 |
| 4,444,570 | 4/1984 | Barth et al. ................ 424/49 |
| 4,496,606 | 1/1885 | Michnowski .............. 426/658 |
| 4,497,832 | 2/1985 | Cherukuri et al. ........ 426/5 |
| 4,554,154 | 11/1985 | White ........................ 424/48 |
| 4,563,345 | 1/1986 | Arrick ....................... 426/3 |
| 4,568,560 | 2/1986 | Schobel ..................... 426/3 |
| 4,572,832 | 2/1986 | Kigasawa et al. ......... 424/435 |
| 4,576,826 | 3/1986 | Liu et al. ................... 426/289 |
| 4,585,657 | 4/1986 | Karwowski et al. ...... 426/285 |
| 4,590,075 | 5/1986 | Wei et al. .................. 426/5 |
| 4,634,598 | 1/1987 | Liu et al. ................... 426/650 |
| 4,639,368 | 1/1987 | Niazi et al. ................ 426/3 |
| 4,673,577 | 6/1987 | Patel ......................... 426/5 |
| 4,749,575 | 6/1988 | Rotman .................... 424/468 |
| 4,752,481 | 6/1988 | Dokuzovic ................ 426/3 |
| 4,824,681 | 4/1989 | Schobel et al. ........... 426/5 |
| 4,832,956 | 5/1989 | Gergely et al. ........... 424/468 |

FOREIGN PATENT DOCUMENTS

| | | |
|---|---|---|
| 829269 | 12/1969 | Canada . |
| 067595 | 12/1982 | European Pat. Off. . |
| 176280 | 4/1986 | European Pat. Off. . |
| 217109 | 4/1987 | European Pat. Off. . |
| 229000 | 7/1987 | European Pat. Off. . |
| 86-3102 | 6/1986 | PCT Int'l Appl. . |
| 86-3676 | 7/1986 | PCT Int'l Appl. . |
| 86-6252 | 11/1986 | PCT Int'l Appl. . |
| 87-543 | 1/1987 | PCT Int'l Appl. . |
| 1060258 | 3/1967 | United Kingdom . |
| 2166651 | 5/1986 | United Kingdom . |

OTHER PUBLICATIONS

McCabe et al., Unit Operations of Chemical Engineering, Second Edition; McGraw Hill Book Company, N.Y., N.Y., Appendix 18.

*Primary Examiner*—Ronald W. Griffin
*Attorney, Agent, or Firm*—Richard Kornutik

[57] ABSTRACT

Active ingredients useful in chewable articles of commerce are physically encased in non-porous, chewable, particles of elastomer and such particles are then incorporated in the articles of commerce. During mastication of the chewable article of commerce the active ingredient is released from the elastomer particles over a prolonged period of time. The active ingredients would include flavorants, intense sweeteners, colorants, medicaments, effervescent agents and tobacco.

44 Claims, No Drawings

4,975,270

ELASTOMER ENCASED ACTIVE INGREDIENTS

BACKGROUND OF THE INVENTION

1. Field of the Invention

The present invention relates to the use of elastomer encased active ingredients in chewable articles of commerce for the purposes of providing a long term release of such active ingredients during the mastication of such articles of commerce.

2. Description of the Prior Art

Various types of chewable articles of commerce are known. They would include those of a comestible or semi-comestible type and those of a mechanical type.

Various types of active agents or ingredients are used in various of these chewable articles of commerce, particularly the comestible or semi-comestible types thereof. Such active ingredients would include flavorants, intense sweeteners, colorants, medicaments and effervescent agents ($CO_2$ or other gas generating systems).

For commercial acceptance purposes, it is often desirable to provide for extended periods of release of such active ingredients from the chewable articles of commerce in which they are used, during the mastication of such products. A technique commonly employed in this regard, is the encapsulation of the active ingredient within a shell of a material designed to provide a complete coating around particles of the active ingredient. Such encapsulation procedures usually require the use of solutions or dispersions of the coating material, and the use of spray drying or drum drying procedures for the application of the coating material to the particles of the active ingredient and/or for the removal of the solvent values from the coated particles.

Such procedures, however, are basically limited to being useful only with those types of coating materials which are readily soluble in one or more solvents and/or those coating systems which can be readily dried without subjecting the active ingredient to any adverse heat or solvation history. Such prior art systems are, for the most part, not useful with elastomers. Further, such prior art encapsulation systems tend to be limited in terms of the length of time that they can delay or extend the release of the active ingredients, i.e., usually only over a period of up to about five to ten minutes, at most. Further, in many cases, where the active ingredient is released from such encapsulating agents it may only be released in a single burst of the active ingredient. Also, each of the prior art means available for encapsulating active ingredients tend to be limited, respectively, in terms of the active ingredients with which they can be used and/or with respect to the chewable products in which they can be employed.

U.K. No. 2,166,651 discloses the use of porous controled release powders having an average particle size in the range of 0.1 to 125 $\mu m$ (microns) which comprise various types of active ingredients in a matrix of nontoxic polymers. The active ingredients are released from the powders by dissolution. The particle sizes are designed to be unaffected by chewing action even though the powders may be used in chewable products.

Prior to the present invention, therefore, it has not been readily possible, if at all, to provide a single non-porous, chewable, carrier means for incorporating a wide variety of active ingredient in a wide variety of the various types of chewable products commercially available, in such a way as to provide for relatively long periods of release of the active ingredient from such products.

OBJECTS OF THE PRESENT INVENTION

An object of the present invention is to provide a wide variety of active ingredients for use in a wide variety of chewable articles of commerce and in a form which provides for a relatively prolonged period of release of such active ingredient during, and by, the mastication of such products.

A further object of the present invention is to provide non-porous, chewable, elastomer encased active ingredients adapted to be useful in a wide variety of chewable articles of commerce.

A further object of the present invention is to provide processes for the production and use of such elastomer encased active ingredients.

A further object of the present invention is to provide novel chewable articles of commerce made with such elastomer encased active ingredients.

SUMMARY OF THE PRESENT INVENTION

It has now been found, according to the present invention, that a wide variety of active ingredients intended for use in a wide variety of chewable articles of commerce can be readily introduced into such articles of commerce so as to provide for a relatively long term release of such active ingredients during the mastication of such articles of commerce if the active ingredients are first encased in non-porous, chewable, particles of elastomer by processes disclosed herein, prior to the introduction of the active ingredient into the article of commerce.

DESCRIPTION OF THE PREFERRED EMBOIDMENT

The chewable articles of commerce are items intended to be chewed or masticated after being orally ingested by man or animals. Such chewable articles of commerce would include those of a comestible type such as antacid tablets, breath protective tablets, taffy-type candy, and dog biscuits; and those of a semicomestible type such as chewing gum, chewing tobacco, and synthetic rawhide type teething devices for canines, and those of a non-comestible or mechanical type such as buccals, boluses, rubber teething devices, athletic mouth pieces, bottle nipples, bits for horses or other animals, and chewable rubber toys for canines and felines.

The comestible or semi-comestible types of chewable articles of commerce are designed to be so completely masticated that they lose their shape during use and a portion or all of the articles is designed to be ingested. In the case of the non-comestible or mechanical chewable articles of commerce they are designed to essentially retain their shape during use, and for the most part, prior to the advent of the present invention, are not usually intended (with the notable exception of the buccals or boluses) for use for the purposes of providing or delivering an active ingredient to the user thereof.

The active ingredients intended for use in the chewable articles of commerce according to the present invention are active ingredients commonly used heretofore in the comestible and semi-comestible types of chewable articles of commerce such as flavoring agents including spices and herbs; sweetening agents, and particularly intense sweeteners; coloring agents; and medicaments, including pharmaceuticals or drugs, minerals, vitamins, (essential) amino acids, aspirin, laxatives and antacids. Additional listings of candidate active ingredients which may be used in the products of the present invention include those listed in U.K. No. 2,166,651 and U.S. Pat. No. 4,639,368, the disclosures of which are hereby incorporated herein by reference.

The active ingredients are preferably used, for the purposes of the present invention, in the form of liquids or solids.

The solid active ingredient materials would have a particle size smaller than that of the elastomer particles, as described below. The solid particles of active ingredients could thus have particle sizes in the range of about 10 to 1000, preferably 25 to 500, and most preferably 50 to 300, micrometers or microns. The liquid active ingredient materials are used in liquid form.

The term elastomer, as used herein, means a material which when stretched under low stress at room temperature ($\sim$20–25° C.) to at least twice its original length, and then upon immediate release of the stress, will return with force to its original length. (McGraw-Hill Dictionary of Scientific & Technical Terms, 2nd E. 1978) The preferred elastomers are food grade elastomers. The elastomers are preferably thermoplastic, but may be cross-linked or thermoset, if they are chewable, i.e., deform, when used in particulate form in chewable articles of commerce as contemplated herein.

The elastomers to be used in preparing the encapsulated active ingredients according to the present invention should, in most cases, be harder than the matrix of the chewable article of commerce in which they are to be used, so that the encapsulated particles of active ingredient retain their structural integrity during the mastication process and do not disintegrate, or otherwise become indistinct, in such matrix. Thus, by retaining their structural integrity in such cases, the non-porous, chewable, particles can serve as minute reservoirs of the active ingredient from which minute doses of the active ingredient can be continuously pumped from their elastomeric encasing agent during the continued mastication thereof. In some cases, however, it may also be desirable for the encasing elastomer to be as soft as, or even softer than, the matrix of the chewable article of commerce in which they are to be used. In such cases the soft(er) particles of elastomer and active ingredient therein, would, when chewed, readily become dissipated, phase-wise, into the matrix of the chewable article of commerce. The particles of encapsulated active ingredient would thus lose their individuality, or structural integrity, and the active ingredient would then be completely dissipated throughout the matrix of the chewable article of commerce. This would be desirable where a more rapid burst of the active ingredient, into such matrix, is desired. This may be desired where the active ingredient is a color additive and it is desired to use such active ingredient to effect a rapid color change or other rapid effect in such matrix. Further, a combination of elastomer encased active ingredients may be used wherein some of the active ingredients are encased in elastomers which are softer than the matrix of the chewable article of commerce, and some of such encasing elastomers are harder than such matrix. Upon masticating a product containing such a combination of elastomer encased active ingredients a substantially sequential release of such active ingredients could be provided, wherein all of the active ingredients could be released first from the softer encapsulating elastomers, while the harder encapsulating elastomers continued to deliver, over a further, extended, period of time, the active ingredient encased therein.

Obviously, the harder the encasing elastomer is, the harder it will be to pump the active ingredient therefrom during the mastication thereof. The use of a plurality of different encapsulating elastomers of varying degrees of softness & hardness &/or various particle sizes, and with various levels of active ingredient loadings therein, therefore, will thus provide for different rates and periods of release of active ingredient therefrom.

The elastomers may be natural or synthetic in nature. A more specific listing of elastomers which may be used in the encased active ingredient compositions of the present invention would include all the natural and synthetic masticatory materials listed below as being useful in the formulation of chewing gum bases.

The elastomer encased active ingredient is prepared by first forming a homogeneous dispersion of the active ingredient in the elastomer by, preferably, admixing the active ingredient into the elastomer which has been placed in molten or malleable form. Plasticizing the elastomer with small amounts, of about 1 to 15 weight %, of liquid active ingredients helps to facilitate the subsequent incorporation of any solid active ingredients therein. Depending on the nature and purpose of the active ingredient, the homogeneous compositions of the present invention will contain a total of about 5 to 70, and preferably about 15 to 40, weight percent of all of the active ingredients to be encased therein, and, optionally, about 1 to 16 weight % of plasticizer, and, optionally, about 1 to 30 weight % of inert filler, with the remainder being the elastomer matrix. One, or a plurality, of the active ingredients can be added to any one batch of such product.

In order to maintain the integrity of the individual particles of elastomer encased active ingredient, relative to each other, during the manufacture and storage thereof, it is desirable to admix with the elastomer and active ingredient a non-humectant, food grade, dusting agent such as talc, sugar, mannitol, calcium carbonate, starch, silica and silicates, which is chemically inert to the elastomer and active ingredient. The dusting agent is used in such amounts as is necessary to effect the desired particle integrity. The softer elastomers tend to be stickier than the harder ones, and would thus require the use of larger amounts of dusting agent therewith. The amounts of dusting agent to be used would range from about 2 to 30, and preferably about 5 to 15, % by weight based on the total weight of the elastomer, active ingredient and dusting agent.

The mixing devices that can be used to admix the elastomer and the active ingredients would include all those high shear mixing devices known to those in the elastomer compounding arts such as Brabender mixers, three roll mixers, Werner Pfliderer and other multi purpose (continuous) extruder mixers. The preferred mixing devices are those containing self-cleaning screws containing conveying and mixing elements.

The amount of shear needed to achieve the desired admixing results will vary depending on the nature and hardness of the elastomer and the amount and type (solid vs liquid) of active ingredient being added thereto.

The admixing of the active ingredient into the elastomer is conducted at temperatures of about 25° to 180° C. The amount of time needed to homogeneously admix the elastomer and active ingredient together will also vary with the nature or type and amounts of each material, and the type of mixing device used. For example, batches of such materials that are extruded at the rate of about 100 pounds per hour through a Werner Pfleiderer extruder having a length to diameter L/D ratio of about 27 would require the use of a specific mechanical energy input of about 0.10 to 0.6 and preferably of about 0.35±0.5 at temperatures in the range of about 25 to 180° C. Any liquid additives that may be blended in with such devices under such conditions are preferably added after a 15 L/D site on the extruder barrel, and all the solid additives are added at the intake end of the barrel.

After the homogeneous mass of dispersed active ingredient and elastomer is prepared it is then ground up to form particles of elastomer, with the active ingredient encased therein, which are about 0.20 to 1.20 (200–1200 μm), and preferably about 0.40 to 0.90 (400–900 μm), millimeters in size. At such particle size, the non-porous particles are chewable, i.e., the elastomeric particles are deformable, and can be pumped, so to speak, to force out the active ingredients encased therein.

To facilitate the grinding process the elastomer encased active ingredient is preferably frozen, or cooled to below its brittle point, at temperatures of −200° F. to −320° F., by being immersed in a liquified inert gas such as nitrogen, helium or carbon dioxide. The particles may also be ground up in adequately cooled or chilled rubber grinding mills.

The particles of elastomer encased and dispersed active ingredient are solid, non-porous, materials which are then dispersed in the chewable product in which they are to be used. In the case of comestible or semi-comestible materials, the particles can be readily admixed into, and with, the other components of the formulations used to prepare such comestibles, during the compounding of such formulations. In the case of the mechanical chewable devices which are usually formed by various forms of thermoplastic molding processes, from a thermoformable molding charge, the particles of elastomer encased active ingredients can be readily incorporated into such moldable charges from which the mechanical chewing devices are formed. The active ingredients are physically encased in the elastomers, and not chemically bound thereto. Although a small, insignificant amount of the encased active ingredients may break the outer surface of the encasing elastomer, the composite particles are essentially non-porous.

When the chewable product of the present invention is masticated, the active ingredient is released from the particles of elastomer in which it is encased over a relatively prolonged period of time due to the fact that they must be mechanically released from the elastomer casing by such mastication activity. Such mechanical release action is a relatively slow process, particularly in view of the fact that the residual or reservoir concentration of active ingredient in the elastomer is reduced over the length of the mastication period. When used in chewing gum, for example, the usual weight percents of active ingredients, in prior art encapsulation or unencapsulated form, are readily released and sensed by the masticator in no more than about one to twenty minutes. When the same amounts of active ingredients are used in chewing gum, in the elastomer encased form of the present invention, the period of time needed to extract such active ingredients from the chewing gum product (as sensed by the masticator thereof) is extended to over 5 to 10 and up to about 75 minutes, depending on the softness or hardness of the encasing elastomer and the particle size of the encapsulated active ingredient.

The rates at which an encased additive can be released, by chewing, from the chewable product containing a given elastomer encased active ingredient composition can be increased by softening the elastomer with a plasticizer, or by adding a filler thereto. The plasticizer and/or filler can be added, for such purposes, to the elastomer before, after, or concurrently with, the additive of the active materials thereto, and prior to the freezing and grinding of the elastomer encased active agent compositions. About 1 to 15 weight % of plasticizer, and about 1 to 30 weight % of filler is used for these purposes, based on the combined weight of plasticizer or filler and elastomer. The plasticizers and inert fillers to be used would include those food grade materials usually employed for such purposes in chewing gum compositions, and are not considered active ingredients.

The active ingredients to be used in a given elastomer encased system should be non-reactive with the elastomer and other active ingredients being employed therewith, under the conditions used to, first, make and store the elastomer encased active ingredient materials, and, second, add the elastomer encased active ingredient to the chewable products in which they are to be used, and to store the resulting chewable products. When the chewable products are chewed the released active ingredients would then be expected to react or function in a way to be expected of such materials under such conditions, i.e., a combination of citric acid and $CaCO_3$ would be expected to react, in the presence of the chewers salvia, and provide $CO_2$, as described in Examples 18–19 below.

A released sweetener, colorant, or flavorant would be expected to provide the usual taste or visual sensations associated therewith, and a released medicament, vitamin or other such material would be expected to be ingested and to function as one would expect of such materials. The active ingredients are preferably water soluble, or otherwise adapted to function as intended, in the saliva. Water insoluble materials such as acid saccharin, aspartame and lake (colorants), however, may also be used as active ingredients in the compositions of the present invention. The active ingredients do not include abrasives.

Because of the relatively small size and amounts of the particles of elastomer used as encapsulating agents that may be needed in mechanical chewing devices of the present invention, it is not believed that they would present a hazard to small children of teething age, even if dislodged by such children from any teething or nipple devices in which they may be used.

The preferred chewable products in which the sweetener composition of the present invention may be used are the comestible and semi-comestible types of products and particularly chewing gum products.

The chewing gum compositions contemplated by the present invention comprise all types of sugar and sugarless chewing gums and chewing gum formulations known to those skilled in the art, including the regular gum, and the bubble gum types. Typical chewing gum compositions comprise a chewing gum base, a modifier, a bulking agent or sweetener, and one or more other additives such as, flavoring agents, colorants and antioxidants. The modifying agents are used to soften, plasticize and/or compatibilize one or more of the components of the gum base and/or of the formulation as a whole.

The chewing gum products of the present invention would have the following general formulation:

| COMPONENT | WEIGHT % OF COMPONENT BROAD RANGE | PREFERRED RANGE |
|---|---|---|
| gum base | 15 to 35 | 20 to 30 |
| gum base modifier | 0 to 5.0 | 0.3 to 3.0 |
| bulk sweetener | 0 to 90 | 40 to 65 |
| elastomer encased active ingredient* | 0.05 to 15.0 | 0.1 to 3.0 |
| fillers | 0 to 35 | 0 to 30 |
| glycerine | 0 to 30 | 0 to 15 |
| Total | 100 | 100 |

*The elastomer encased active ingredient would be used in the chewing gum products in such amounts as to provide such chewing gum products with the following amounts of active ingredients encased therein:

| | Weight % of Active Ingredient to Be Formulated (In Encased Form) | |
|---|---|---|
| Active Ingredient | Broad Range | Preferred Range |
| colorant + | 0 to 3.0 | 0.03 to 1.0 |
| flavorant | 0.05 to 2.0 | 0.5 to 1.5 |
| intense sweetener + | 0 to 0.75 | 0.10 to 0.30 |
| vitamin (1)+ | 0 to 1.00 | 0.25 to 0.75 |
| pharmaceutical (2)+ | 0 to 2.00 | 0.50 to 1.00 |

+ = optional component in chewing gum
(1) same amounts for minerals and essential acids
(2) same amounts for aspirin, laxative and antacids

GUM BASE

The composition of the gum base will vary depending on whether the gum base is to be used in a chewing gum product which is to be a regular, or non-bubble, gum product or a bubble gum product. For use in making a bubble gum or regular chewing gum product, the following gum base formulations may be used, in accordance with the present invention:

| | WEIGHT % OF COMPONENT IN GUM BASE FOR | | | |
|---|---|---|---|---|
| | BUBBLE GUM PRODUCT | | REGULAR GUM PRODUCT | |
| COMPONENT | Broad Range | Preferred Range | Broad Range | Preferred Range |
| masticatory material | 8–22 | 9–18 | 8–25 | 9–18 |
| plasticizer for masticatory material | 5–35 | 10–20 | 2–30 | 8–20 |
| hydrophilic detackifier | 0–30 | 4–10 | 5–35 | 10–25 |
| plasticizer for hydrophilic detackifier | 0–14 | 0–8 | 1–15 | 3–12 |
| wax | 3–15 | 5–10 | 4–20 | 8–15 |
| mineral filler | 0–35 | 10–22 | 0–35 | 15–30 |
| antioxidant | 0–0.1 | 0.05–0.09 | 0–0.1 | 0.03–0.09 |
| Total | 100 | | 100 | |

The masticatory substances are elastomeric materials which may be synthetic or natural in origin. The masticatory substances of synthetic origin would include styrene-butadiene copolymer (SBR), butyl rubber (which is isobutylene-isoprene copolymer) and polyisobutylene. The natural masticatory substances should include chicle, crown gum, nispero, balato, jetulong, pendare, perillo, niger, gutta, tunic, leche caspi, sorva and gutta hank kang.

The plasticizer for the masticatory substance should have minimal tackifying properties and will preferably comprise a hydrogenated ester gum, that is a glycerol ester of hydrogenated resin and/or dimerized ester gum. However, other resins may be employed such as pentaerythritol ester gum, polymerized ester gum, polyterpene resin and ester gum.

The hydrophilic-type detackifier is a material which will absorb saliva and would include vinyl polymers having a molecular weight of at least 2000, and preferably of about 2000 to 80,000 or more, such as polyvinyl acetate, polyvinyl butyl ether and copolymers or vinyl esters and vinyl ethers. The plasticizers for the hydrophilic type detackifiers would include lanolin, stearic acid and sodium stearate.

The plasticizers for the hydrophilic type detackifiers would include triacetin, acetylated glycerides and other flavor adjuvants such as ethyl acetate and triethyl citrate.

The waxes which are used serve primarily as compatibilizers. Examples of appropriate waxes are paraffin wax, candelilla wax, carnuba wax, microcrystalline waxes and polyethylene waxes.

The mineral fillers would include calcium carbonate, titanium dioxide, talc, alumina, magnesium hydroxide, dicalcium phosphate, tricalcium phosphate and mixtures thereof, although calcium carbonate is not preferred when saccharin acid is used.

The gum base may also include a softening agent and lubricant combination which may comprise one or more hydrogenated vegetable or animal fats.

The gum base may also include about 0 to about 2.0%, and preferably about 0.1 to about 0.7% of an emulsifier to impart hydrophilic properties to the gum base. Examples of such emulsifiers includes phosphatides such as lecithin, in addition to that used in the gum base modifier, and mono-and diglycerides of these fatty acids and mixtures thereof, with glyceryl monostearate being preferred.

In addition, the gum base may include antioxidants such as butylated hydroxy toluene, butylated hydroxy anisole and propyl gallate.

The chewing gum compositions of the present invention can be sugar based or sugarless. The sugar or sugar substitute used in the compositions of this invention include natural sugars or non-sugar sweeteners. The amount of natural sugars which can be present in the final composition can range from 0 to about 90 weight percent. The amount of non-sugar sweetener which can be used can range from 0 to about 2 weight percent of the final composition. At least one of such sweeteners is employed.

The term "natural sugar" includes one or more sugar containing materials, for example, monosaccharides of 5 to 6 carbon atoms, such as glucose, arabinose, xylose, or sorbose or mixtures of two or more of the foregoing monosaccharides; disaccharides such as sucrose, lactose, maltose or cellobiose; and polysaccharides such as dextrin, or corn syrup solids.

The intense sweeteners include poorly water-soluble, as well as water-soluble sweeteners, such as the free acid form of saccharin, sodium, calcium or ammonium saccharin salts, aspartame (L-aspartyl-L-phenylalanine methyl ester), dihydrochalcones, glycyrrhizin, dipotassium glycyrrhizin, glycyrrhizic acid/ammonium salt, talin, acesulfame K, as well as *Stevia rebandianna* (Stevioside), *Richardella dulcifica* (Miracle Berry), *Dioscoreophylim cumminisii* (Serendipity Berry), free cyclamic acid and cyclamate salts and the like, or mixtures of any two or more of such materials.

The chewing gum made by this invention can also contain conventional FD&C and natural coloring agents.

The flavoring which can be included in the chewing gum compositions made according to this invention can comprise one or more natural and/or synthetic flavors and/or oils derived from plants, leaves, flowers and fruit. Representative flavors and oils of these types include acids such as adipic, succinic and fumaric acid; citrus oils such as lemon oil, orange oil, lime oil and grapefruit oil; fruit essences, such as apple essence, pear essence, peach essence, strawberry essence, apricot essence, raspberry essence, cherry essence, plum essence, and pineapple essence; essential oils such as peppermint oil, spearmint oil, mixtures of peppermint oil and spearmint oil, clove oil, bay oil, anise oil, oil of nutmeg, oil of sage, oil of bitter almonds, cassia oil and methylsalicylate (oil of wintergreen). Various synthetic flavors, such as those for a mixed fruit, may also be incorporated in the chewing gum with or without conventional preservatives.

The above noted non-sugar, or intense, sweeteners, coloring agents and flavorants are examples of specific active ingredients that may be used in the chewing gum products of the present invention in the form of the elastomer encased active ingredients of the present invention. In forming the encased active ingredients one, or a plurality, of such active ingredients may be encased in the same or different particles of elastomers, as otherwise disclosed above.

PREPARATION OF CHEWING GUM PRODUCT

The chewing gum products of the present invention are prepared by first separately preparing the gum base. To then prepare either a sugar based or sugarless chewing gum formulation, the gum base for the product is melted, at a temperature about 190° to 250° F., and the other components of the composition are added thereto. The resulting composition is uniformly admixed. This takes about 3 to 7 minutes for each of the respective components used in commercial sized batches of these formulations. Each of the components is usually separately added to the formulated composition and uniformly mixed in before the next component is added. All of the admixing operations are conducted at temperatures in the range of about 112° to 185° F., and preferably about 125° to 180° F. for a total mixing time, at such temperatures, of about 10 to 25 minutes. The operations do not have to be conducted under anhydrous conditions in preparing the compositions of the present invention, and any amounts of moisture that are normally present in the raw materials that are used in the compositions of the present invention do not usually have to be removed therefrom either prior to, or during, the formulating process.

The elastomer encased active ingredients of the present invention are preferably added at the end of the formulation process to avoid any premature mastication type action thereon which might otherwise occur during the mixing operations.

The following examples are merely illustrative of the scope of the present invention and are not intended as a limitation upon the scope thereof.

The molecular weight values given for the polyisobutylene materials used in the examples are Staudinger viscosity average molecular weight values.

EXAMPLES 1 to 4

A series of four (4) different colorants were separately encased in polyisobutylene elastomer (PIB-120). The elastomer had a molecular weight of about 108,000°±9000°. It was not plasticized, and was semi-transparent. In each example, a Brabender plasticorder mixer with roller blades was preheated to 60°–65° C. and 60 grams of the elastomer was added thereto to soften it over a period of about 10 minutes Brabender mixing time. Then 4 grams of the respective colorant and 10 grams of powdered sodium saccharin having a particle size of about 75 μm (0.0029 inch) was added to the elastomer and homogeneously blended in over a period of about 10 minutes. The resulting homogeneous mixture was then removed from the Brabender mixer, cooled to room temperature (~25° C.), diced into pieces about ⅜ inch on a side and frozen under liquid nitrogen (at −320° F.) and then ground once in a Fitzpatric Mill to form discrete particles of elastomer in which particles of the colorant and Na saccharin were encased. The pieces or particles of elastomer were about 425 μm (0.0165") to 850 μm (0.0331") in size.

The four colorants used were all approved for food and drug use and were yellow #5 HT; orange in the form of yellow #6 HT; FD&C Blue #1 and Red #3. The colorants were all water insoluble lakes and in particulate form, such that about 95.5% had an average particle size of about 38 μm (0.0015") to 45 μm (0.0017"). They were all lakes having a pure dye content in the range of about 15 to 40%.

The colored particles were visible through the encasing skin of the elastomer. The encased particles of Na saccharin were not so visible.

For further use, as noted in Example 5 below, the encased particles of each of the Example 1–4 compositions were separately sieved through a #30 US sieve onto a #40 US sieve so as to recover particles having an average particle size of about 500 μm (0.0197") to 600 μm (0.0234").

EXAMPLE 5

A bubble gum product was prepared which contained samples of each of the four elastomer encased color systems of Examples 1–4.

The formulation of the bubble gum product was as follows:

| Component | Weight % of Component |
|---|---|
| polyisobutylene based gum base containing about 25% CaCo3 filler | 21.50 |
| sugar | 60.60 |
| corn syrup, 43° Be | 10.00 |
| high fructose corn syrup | 6.00 |
| Fruit oil flavor | 0.90 |
| 0.25 weight % of each of the four yellow, orange, blue and red elastomer encased colorants of Examples 1–4 | 1.00 |
| | 100.00 |

A seven kilogram batch of the chewing gum product was made by melting the gum base, cooling it to about 135° F. and then blending the other components therein in conventional chewing gum mixing equipment at 135° F. to 110° F. (final temperature).

The product was then processed into pillow shaped pieces of gum which measured about ⅝"×⅝"×⅜". The colored specks of the encased colorant were visible at the surface of the product, and were evenly distributed throughout the mass thereof.

When the pieces of gum were chewed, and bubbles blown therefrom, the colored particles were separately visible in the bubble's film as individual specks of yellow, orange, red and blue colors. The respective color specks retained their integrity when the gum was chewed over a period of about 60 minutes. The specks did not streak within this 60 minute period of chewing.

A prolonged sweetening effect was achieved over an additional 30 minute chewing period, during which period substantial amounts of the encased sodium saccharin was slowly released from the elastomer particles in which it was encased.

EXAMPLES 6-10

A series of five different polyisobutylene (PIB) encased colorant systems were prepared. There systems were designed to provide encased colors that would streak more readily when used in chewing gum, as compared to the non-streaking capabilities of the color systems prepared in Examples 1-4 above.

The formulations used were as follows, to make about 30-75 gram batches of the respective compositions:

| Component | Example 6 | 7 | 8 | 9 | 10 |
|---|---|---|---|---|---|
| | Grams of Component Used | | | | |
| Elastomer | | | | | |
| PIB L-80 | 20 | — | — | — | — |
| PIB LM-MH | 10 | — | — | — | — |
| PIB 100 | — | 30 | 30 | 30 | 34 |
| PIB (Plas) | — | 20 | 10 | 25 | — |
| Colorant | | | | | |
| Red #3 | — | 2 | — | 2 | — |
| Blue #1 | — | 0.5 | — | — | — |
| Yellow #6 | — | — | 2 | — | — |
| Red #3 | 0.05 | — | — | — | 0.9 |
| Intense Sweetener | | | | | |
| Na saccharin | — | — | — | 10 | — |
| Aspartame | — | — | — | — | 17 |
| Filler | | | | | |
| Talc | — | — | — | — | 12 |
| Flavorant | | | | | |
| Fruit oil | — | — | — | — | 11 |

The elastomers used were all semi-transparent polyisobutylene materials. PIB-L-80 has a molecular weight of about 64,000-81,000 and PIB-LM-MH has a molecular weight of about 10,000 to 11,700, so that the average molecular weight of the PIB blend of Example 6 was about 40,000. The low molecular weight non-elastomeric PIB-LM-MH acted as a plasticizer for the elastomeric PIB L-80. PIB(Plas) is a compounded form of PIB-100 which has been plasticized by being admixed with about 5% by weight of glycerol ester of hydrogenated resin (Stabelite Ester #5). PIB-100 has a molecular weight of about 81,000 to 99,000.

The colorants are the same as those used in Examples 1-4. The aspartame and sodium saccharin was used in particle form, about 75 μm (0.0029") in average particle size. The talc was used in particle form, about 53 to 63 μm (0.0021 to 0.0025") in average particle size.

The procedure used to separately make each of the Example 6-10 elastomer encased colorant products was similar to that of Examples 1-5.

For each Example a Brabender mixer was preheated to about 65° C. and the elastomer(s) material(s) were added thereto to soften it over a period of about 10 minutes of Brabender mixing time. The colorant and intense sweetener (where the latter was used) were then added slowly over about an eight (8) to ten (10) minute period, and were then admixed with the elastomer for about another ten minutes or until the admixed composition was continuous. Where used, the flavor and filler was then added and the composition was admixed about another ten minutes, until continuous. The resulting composition, which had a homogeneous or continuous appearance, was then removed from the Brabender mixer, cooled to room temperature, diced into cubed pieces about ⅜" on each side, and frozen under liquid nitrogen, and then ground in a Fitzpatric mill to form discrete particles of elastomer in which particles of the various additives were encased. The particles of the elastomer were about 500 μm (0.0197") to 1 mm (0.0394") in size. The particles of the colorants were visible through the surface of the encasing elastomer, the particles of the other additives including the talc, were not visible.

For further use, as noted in Example 11 below, the resulting encased particles of the Example 6-10 compositions were each separately sieved through a #30 U.S. sieve onto a #40 U.S. sieve so as to recover particles having an average particle size of about 500μm to 600 μm.

EXAMPLES 11-15

Each of the Examples 6-10 elastomer encased particulate compositions were separately used at a 1.0% weight level in the chewing gum formula of Example 5 (in lieu of the 1% of the multi color additive originally used in the Example 5 formulation).

A seven kilogram batch of chewing gum was thus made with each of such Examples 6-10 elastomer encased additive systems, by first melting the gum base, cooling it to about 138° F., and then blending the other components therein together in conventional chewing gum mixing equipment at 138° F. to 110° F. (final temperature).

The resulting five chewing gum products were then each separately processed into cube shaped pieces of gum which measured about ⅝"×⅝"×⅜". The colored specks of the encased colorant were visible in each product at the surface thereof, and were evenly distributed throughout the mass thereof. The particles of the other additives, where used, were not evident to the naked eye.

When pieces of each of these chewing gum products were separately chewed, and bubbles blown therefrom, the colored particles were, initially, separately visible in the bubble's film as individual specks of yellow, orange, red and blue colors, where used. Upon chewing these products for only about 2 to 15 minutes, however, the colors began to readily streak and to run into each other.

The presence of the intense sweeteners used in the Example 9-10 compositions also became evident after chewing times of about 2 to 15 minutes.

The effect of the filler in the Example 10 composition was evidenced, upon the chewing of the gum, by the fact that its presence increased the release rate of the APM, and thus shortened its release time from 40 minutes (for the Example 16 material) to 30 minutes.

The effect of the flavor in the Example 10 composition was evidenced, upon the chewing of the gum, by the fact that the perceived fruit flavor level was higher after two minutes chewing time for the Example 10 material, than for the Example 6-9 chewing gum products.

EXAMPLE 16

A delayed release coloring system was prepared in this Example, using the following components:

| Amount of Component | Component |
| --- | --- |
| 90.0 grams | PIB-L-80 elastomer |
| 6.0 grams | aspartame |
| 4.5 grams | purple colorant |

The non-elastomeric additive components were all in particulate form, having a particle size of about 75 μm (0.0331"). The purple colorant is formed from a blend of Red #3 & Blue #1 lakes.

The elastomer encased additive system was made as in Examples 1-4 above. A Brabender plasticorder was preheated to 60° to 65° C. and the elastomer added thereto to soften it over a period of about 10 minutes mixing time. Then the aspartame was added and mixed in for about 10 minutes to achieve a homogeneous distribution of the APM in the elastomer. The colorant was then added and mixed in for about 10 minutes to achieve a homogeneous blend. The color of the colorant at this point was evident to the naked eye.

The resulting mixture was then removed from the Brabender mixer, diced into cubed shaped pieces about ⅜" on a side, frozen in liquid nitrogen, and then ground in a Fitzpatric mill to form discrete particles of elastomer in which particles of the APM and colorant were dispersed.

About 5% by weight of particulate $TiO_2$ (white pigment powder grade) was added to the frozen elastomer as it was being ground to act as a color masking agent and to maintain the individual integrity of the ground particles of the elastomer.

The resulting particles were sieved through a #18 U.S. mesh screen (1000 μm) and onto a #20 U.S. mesh screen (850 μm) so as to retain those particles having a particle size of about 850 to 1000 μm.

The presence of the dusting agent will mask the color of the colorant in the unchewed and chewed gum, until it is washed off by saliva during chewing of the gum - which will take about 1-5 minutes depending on the amount of dusting agent used.

EXAMPLE 17

A bubble gum product was prepared with the delayed release colorant system of Example 16, using the following formulation:

| Component | Weight % of Component |
| --- | --- |
| polyisobutylene based gum base containing about 25% Talc as filler | 22.50 |
| sugar | 59.60 |
| corn syrup 43° Be | 10.00 |
| high fructose corn syrup | 6.00 |
| Fruit oil flavor blend | 0.90 |
| elastomer encased colorant of Example 16 | 1.00 |
| | 100.00 TOTAL |

A 2 kilogram batch of the chewing gum product was made by melting the gum base, cooling it to about 138° F., and then blending the other components therein in conventional chewing gum mixing equipment at 138° F. to 110° F. (final temperature).

The product was then processed into cubed shaped pieces of gum which measured about ⅜"×⅜"33 ⅞". The particles of encased colorant were not visible to the naked eye.

When the pieces of gum were chewed and bubbles blown therefrom, there was, initially, little visible evidence of the presence of the colored particles, either as visible specks or as streaks. After about 5 minutes of chewing time, however, the color of the gum, and the bubbles blown from it, had a violet background color in which purple specks were evident.

The APM was released from the unplasticized PIB-L-80 elastomer particles, during chewing of the gum of this example, over a period of about 25-35 minutes. This rate of release is slower then if this elastomer had been plasticized, and is faster than the rate of release observed for the chewing gum containing an intense sweetener encapsulated in a higher molecular weight PIB elastomer (of Example 21 below).

EXAMPLE 18

An elastomer encased effervescent or $CO_2$ gas generating system was prepared in this Example, using the following components:

| Amount of Component | Component |
| --- | --- |
| 40 grams | PIB-L-80 elastomer |
| 2 grams | aspartame |
| 10 grams | citric acid |
| 10 grams | calcium carbonate |
| 0.5 grams | red #3 lake (37% dye content) |
| 62.5 grams | TOTAL |

The non-elastomeric additive components were all in particulate form having a particle size in the range of about 38 μm to 90 μm. The citric acid and $CaCO_3$ were preblended, dry, together.

The elastomer encased additive system was made as in Example 16 above. The Brabender plasticorder mixer was preheated to 60°-65° C., and the elastomer added thereto to soften it over a period of about 10 minutes. Then the aspartame and colorant was added and mixed in for about 10 minutes to achieve a homogeneous distribution of the APM in the elastomer. The premixed blend of citric acid and $CaCO_3$ was then added and mixed in for about 10 minutes to achieve a homogeneous distribution of these materials in the elastomer. Specks of the red colorant were evident to the naked eye, and evenly distributed throughout.

The resulting mixture was then removed from the Brabender mixer, diced into pillow shaped pieces about ⅜ inch on a side, frozen in liquid nitrogen, and then ground in a Fitzpatric mill to form discrete particles of elastomer in which particles of all the additives were evenly dispersed. The colorant particles was visible to the naked eye.

The resulting particles were then sieved through a #18 U.S. mesh screen and retained on a #20 U.S. mesh screen so as to retain those particles having a particle size of about 900 μm.

EXAMPLE 19

A bubble gum product was prepared with the effervescent agent system of Example 18, using the following formulation:

| Component | Weight % of Component |
|---|---|
| polyisobutylene based gum base containing about 25% Talc filler | 22.50 |
| sugar | 59.60 |
| corn syrup, 43° Be | 10.00 |
| high fructose corn syrup | 6.00 |
| Fruit oil flavor blend | 0.90 |
| effervescent agent of Example 18 | 1.00 |
| TOTAL | 100.00 |

A 2 kilogram batch of the chewing gum product was made by melting the gum base, cooling it to about 125° F., and then blending the other components therein in conventional chewing gum mixing equipment at 125° to 115° F. (final temperature).

The product was then processed into pillow shaped pieces of gum which measured about $\frac{3}{8}'' \times \frac{3}{8}'' \times \frac{3}{8}''$. The particles of encased colorant were visible, but not the particles of the other encased additives.

When the pieces of gum were chewed and bubbles blown therefrom, red specks of colorant were readily visible immediately, and upon prolonged chewing, of about 5 to 10 minutes, the specks began to streak.

During the initial 5 minutes of chewing, a pronounced fizzing effect was noted in the mouth of the chewer as the $CaCO_3$ and citric acid were released from the elastomer encasing and reacted to form $CO_2$.

An extended period of sweetness was perceived for the APM, of about 10 to 20 minutes of chewing time.

COMPARISON EXAMPLE 20

For comparison purposes particulate Na saccharin, having a particle size of about 63 to 90 μm, was encapsulated in polyethylene using the encapsulating techniques disclosed in U.S Pat. No. 4,384,004. Using such procedures 40 weight % of Na saccharin was encapsulated in 60 weight% of polyethylene. The resulting compositions were particles having an average particle size of about 90 to 180 μm.

EXAMPLE 21

Sodium saccharin having a particle size of about 63 to 90 μm was encapsulated in polyisobutylene (PIB-120) as follows:

A Brabender mixer was preheated to about 60° C. and 30 grams of the elastomer was mixed in and softened in the mixer for about 5 minutes. The Na saccharin (10 grams) was then added and mixed for 20 minutes to provide a homogeneous blend. This procedure was followed a total of five times, and the five batches of encapsulated Na saccharin were then blended together.

The resulting composite mixture was then diced into pillow shaped pieces about ⅜ inch on a side, frozen in liquid nitrogen, and then ground in a Fitzpatric mill to form discrete particles (0.25") of the elastomer in which particles of the Na saccharin were evenly dispersed, but not visible to the naked eye. Talc (about 50 grams) was added as a dusting agent to eliminate clumping of the Na saccharin encapsulated particles. It did not become part of the matrix of the particles. The particles were again then refrozen in liquid $N_2$ and reground again through a #2A mesh screen (0.093").

The resulting particles were further sieved through a #25 U.S. mesh screen and onto a #30 U.S. mash screen, so as to retain particles having a particle size of about 710 μm.

EXAMPLES 22-23

The prolonged sweetness release characteristics of the two forms of encapsulated Na saccharin made in Examples 20 and 21 were compared in these Examples. The encapsulated Na saccharin materials were formulated into chewing gum of the following composition:

| Component | Example 22 weight % of component | Example 23 weight % of component |
|---|---|---|
| styrene-butadiene based gum base | 26.9 | 26.9 |
| crystalline sorbitol | 46.4 | 46.7 |
| cooked hydrogenated starch hydrolysate | 24.5 | 24.5 |
| peppermint flavor | 1.2 | 1.2 |
| lecithin | 0.7 | 0.7 |
| (0.12%) PE encap. Na saccharin of Ex. 20 | 0.30 | — |
| (0.16%) elastomer encased Na saccharin of Ex. 21 of 710 μm particle size | — | 0.08 |
| | 100.00 | 100.08 |

A 2 kilogram batch of each of the chewing gum products of such Example 22 and 23 formulations was similarly made by melting the gum base, cooling it to about 180° F., and then blending the other components therein in conventional chewing gum equipment at 180° to 110° F. (final temperature).

The two respective products were then processed into stick shaped pieces of gum which measured 0.067 $'' \times \frac{3}{4}'' \times 2\frac{7}{8}''$. The particles of encased Na saccharin were not visible to the naked eye in either product.

Pieces of each chewing gum product were then comparatively chewed and evaluated by a panel of nine (9) panelists. The panelists were presented with blind coded samples of the two products in a balanced randomized order. Seltzer water and Premium brand unsalted Saltine Crackers were provided for mouth conditioning during a one hour rest period provided between the testing of each replication of the test procedure. Aqueous sucrose solutions of 2%, 5%, 10%, 15% & 20%, by weight, were provided as reference anchors.

Each panelist chewed a piece of gum representing each of the two test products for a period of 60 minutes. The chewing tests for each product were run three times for each product. The panelist evaluated the sweetness of the respective products, numerically, using a scale of numerical ratings from 0 to 200, wherein the value 0 represents the lowest possible rating for perceived sweetness and the value 200 represents the highest possible rating for perceived sweetness, and the numerical values between 0 and 200 represent progressively higher values for perceived sweetness, i.e. 0 for no perception, 50 for slight perception, 100 for moderate perception, 150 for strong perception and 200 for extreme perception. The perceived sweetness values were recorded by the panelists, at intervals of 30 seconds each over the first two minutes of test time, thereafter, at intervals of one minute each over the next eight minutes of test time, and, thereafter, at intervals of two minutes each over the remainder (50 minutes) of the test time. The numerical ratings assigned by the test panelists to the two products so tested, with the p-values and significance, thereof, is noted in Table I below. The p-values and significance thereof relative to the tests in question are based on standard statistical analysis techniques.

The Table I test results indicate that the Control product of Example 22 provided a strong to significantly higher level of sweetness only during the 2 to 4 minute term of the test period, whereas the product of the present invention, that of Example 23, provided a (strong to very significantly) higher level of sweetness during the prolonged 14 to 40 minute term of the test period.

The quicker up-front release of the sweetener of Control Example 22 also indicates that the product will have significantly less sweetener available for any attempted prolonged chewing period.

TABLE I

SWEETNESS EVALUATION OF EXAMPLES 22 & 23
Chewing Gum Product

|  | Example 22 Product | Example 23 Product | P-Value | Sig. |
|---|---|---|---|---|
| 30 sec. | 142.7 | 136.2 | .2970 | NS |
| 1 min. | 157.4 | 151.9 | .2151 | NS |
| 1½ mins. | 160.8 | 155.2 | .2090 | NS |
| 2 mins. | 153.8 | 143.0 | .0674 | Strong trend |
| 3 mins. | 135.9 | 125.8 | .0250 | * |
| 4 mins. | 113.9 | 105.3 | .0679 | Strong trend |
| 5 mins. | 95.6 | 90.7 | .3403 | NS |
| 6 mins. | 78.6 | 76.6 | .7198 | NS |
| 7 mins. | 67.1 | 66.6 | .9818 | NS |
| 8 mins. | 57.8 | 61.2 | .4380 | NS |
| 9 mins. | 51.5 | 54.9 | .4151 | NS |
| 10 mins. | 45.6 | 48.9 | .3997 | NS |
| 12 mins. | 37.4 | 44.4 | .0801 | trend |
| 14 mins. | 32.0 | 39.9 | .0531 | Strong trend |
| 16 mins. | 28.5 | 35.4 | .0631 | Strong trend |
| 18 mins. | 23.6 | 32.1 | .0044 | ** |
| 20 mins. | 17.4 | 28.7 | .0014 | *** |
| 22 mins. | 15.4 | 23.7 | .0029 | ** |
| 24 mins. | 12.6 | 20.7 | .0051 | ** |
| 26 mins. | 9.3 | 15.6 | .0105 | ** |
| 28 mins. | 7.6 | 12.7 | .0282 | * |
| 30 mins. | 5.2 | 9.4 | .0540 | Strong trend |
| 32 mins. | 3.6 | 7.4 | .0467 | * |
| 34 mins. | 1.3 | 5.1 | .0072 | ** |
| 36 mins. | .5 | 4.2 | .0064 | ** |
| 38 mins. | .04 | 3.0 | .0195 | * |
| 40 mins. | .04 | 2.3 | .0251 | * |
| 42 mins. | .04 | .9 | .2694 | NS |
| 44 mins. | .7 | .65 | .9108 | NS |
| 46 mins. | .41 | .54 | .8913 | NS |
| 48 mins. | .41 | .54 | .8913 | NS |
| 50 mins. | .63 | 0 | .3118 | NS |
| 52 mins. | 0 | 0 | — | — |
| 54 mins. | 0 | 0 | — | — |
| 56 mins. | 0 | 0 | — | — |
| 58 mins. | 0 | 0 | — | — |
| 60 mins. | 0 | 0 | — | — |

* sig. at .05 level
** sig. at .01 level
*** sig. at .001 level
Sig. = significance
sig. = significant
NS = not significant The initial short-burst sweetness trends shown in Table I for the 2 to 4 minute test period are for the product of Control Example 22, whereas the prolonged delayed release trends shown for the 12 to 40 minute test period are for the product of Example 23, that of the present invention.

Similar prolonged sweetness results were achieved according to the teachings of the present invention in chewing gum products made as in Example 23 but wherein the intense sweetener, sodium saccharin or aspartame, at a loading of about 20 to 33% of intense sweetener, was encapsulated in elastomers other than polyisobutylene, such as styrene butadiene elastomer and butyl rubber, using the encapsulation procedure generally as described in Example 21.

Similar prolonged sweetness results were also achieved according to the teachings of the present invention in chewing gum products made as in Example 23 but wherein the sodium saccharin was admixed with acid saccharin in a 1 to 1 weight ratio, using the procedure generally as described in Example 21.

A filler such as talc or $CaCO_3$, at a loading of about 10–25%, was also encapsulated with one or more of such intense sweeteners to further modify the release of the sweetener from the elastomer encapsulated systems, as they were masticated in the chewing gum products in which they were formulated. The higher filler loadings provided for a faster release of the active agent.

EXAMPLE 24

A sweetened, and peppermint oil and tobacco flavored, chewing gum product was produced according to the present invention.

A commercial unflavored chewing tobacco product was frozen in liquid nitrogen (to facilitate grinding) and then ground up in a micropulverizer using a 1/16″ screen to provide particles thereof that passed through a #40 U.S. screen (0.0165″ or 425 μm).

A Brabender plasticorder mixer with roller blades was preheated to 60°–65° C. and 30 grams of polyisobutylene (of 81,00–99,000 molecular weight) was added thereto to soften it over a period of about 10 minutes mixing time. Then the shredded tobacco (19 grams) was added to the elastomer and blended in uniformly over a period of about 10 minutes. Then 2.5 grams of asparatame and 6 grams of peppermint oil flavorant were added slowly and blended into the admixture, and mixed in for an additional mixing time of about 10 minutes. Twenty (20) grams of talc were added after the first grinding to the ground particles to prevent clumping thereof.

The resulting homogeneous admixture was then removed from the Brabender mixture, diced into cubed shaped pieces about ⅜ inch on a side and frozen under liquid nitrogen and then ground in a Fitzpatric mill using a #4 Screen (0.25″) to form discrete particles of elastomer in which particles of the tobacco, APM and peppermint flavorant were encased. These particles were refrozen in liquid nitrogen and reground in a second pass through the Fitzpatric mill with a #2A screen (0.093″) so as to provide particles between 425 μm and 1000 μm in size. The resulting particles were then further sieved through a #16 U.S. mesh screen (1.18 mm) and separate portions thereof were collected on #20 (850 μm), #25 (710 μm) and #30 (600 μm), U.S. mesh screens.

The various particle sizes of the resulting products provide different release rates, when used in masticated end products. The larger sized particles provide for the more prolonged periods of release of the various additives used therein.

EXAMPLE 25

A bubble gum product was prepared which contained a sample of the elastomer encased tobacco based flavorant of Example 24. The formulation of the bubble gum product was as follows:

| Component | Weight % of Component |
| --- | --- |
| polyisobutylene based gum base containing about 25% $CaCO_3$ filler | 24.00 |
| sugar | 54.50 |
| corn syrup, 43° Be | 14.00 |
| high fructose corn syrup | 2.50 |
| Lecithin | 0.20 |
| peppermint oil | 1.00 |
| elastomer encased flavorant of Example 24 of a blend of particles 600–850 μm particle size | 3.80 |
| | 100.00 |

A one kilogram batch of the chewing gum product was made by melting the gum base, cooling it to about 135° F., and the blending the other components therein in conventional chewing gum mixing equipment at 135° F. to 110° F. (final temperature).

The product was then processed into cube shaped pieces of gum which measured about ⅜"×⅜"×⅜". The particles of additives were not visible to the naked eye at the surface of the product, and were evenly distributed throughout the mass thereof. The particles retained their individual integrity as evidenced by being observable to the touch and eye in very thin slices of the chewing gum product.

When the pieces of gum were chewed (& bubbles blown therefrom) the tobacco flavor was evident over a period of about 45 minutes chewing time. This perceived flavor was from saliva soluble fractions of the tobacco, and not from solid pieces of the tobacco.

The presence of sweetness from the APM, and the peppermint oil flavor, could also be detected after about 30 minutes chewing time.

What is claimed is:

1. A solid non-porous, chewable, particle of a food grade elastomer based encapsulating composition, said encapsulating composition being a water insoluble elastomer selected from the group consisting of polyisobutylene, butyl rubber, styrene butadiene, rubber, chicle, crown gum nispero, balato, jetulong, pendare, perillo, niger, gutta, tunic, leche caspi, sorva, and gutta hank kang and having encased therein one or more active ingredients employed in chewable products, and solid particle of encapsulating composition having a particle size of about 200 to 1200 microns and said active ingredient being in the form of a liquid or a solid and when in solid form having a particle size less than that of said particle of encapsulating composition and being about 10 to 1000 microns, said active ingredient being encased in said solid particle of encapsulating composition so as to facilitate and release of said active ingredient over a prolonged period of time in a chewable environment.

2. A solid particle as in claim 1 which has a particle size of about 400 to 900 microns.

3. A solid particle as in claim 1 in which said elastomer is plasticized with about 1 to 15 weight % of one or more food grade plasticizers therefor.

4. A solid particle as in claim 1 which further comprises about 1 to 30 weight % of one or more food grade fillers.

5. A solid particle as in claim 1 in which said active ingredient is selected from the group consisting of intense sweeteners, colorants, flavorants, medicaments, tobacco and effervescent agents.

6. A chewable product having extended active ingredient release characteristics and comprising at least one active ingredient therefor physically encapsulated in non-porous, chewable, particles of a water-insoluble elastomer selected from the group consisting of polyisobutylene, butyl rubber, styrene butadiene rubber, chicle, crown gum, nispero, balato, jetulong, pendare, perillo, niger, gutta, tunic, leche caspi, sorva, and gutta hank kang, said solid particles of elastomer having a particle size of about 400 to 900 microns and said active ingredient being in the form of a liquid or a solid and when in solid form having a particle size less than that of said solid particles of elastomer and being about 25 to 500 microns, said active ingredients being encapsulated in said solid particle of elastomer so as to facilitate the release of said active ingredient over a prolonged period of time when said product is chewed.

7. A chewable product as in claim 6 selected from comestible, semi-comestible and non-comestible products.

8. A chewable product as in claim 7 which is a comestible product.

9. A chewable product as in claim 7 which is a semi-comestible product.

10. A chewable product as in claim 7 which is a non-comestible product.

11. A chewable product as in claim 9 which is chewing gum.

12. A chewable product as in claim 9 which is chewing gum and said active ingredient comprises as least one intense sweetener.

13. A chewable product as in claim 12 in which said active ingredient comprises aspartame.

14. A chewable product as in claim 12 in which said active ingredient comprises saccharin.

15. A chewable product as in claim 12 which is chewing gum and said active ingredient comprises as least one colorant.

16. A chewable product as in claim 15 in which said colorant is adapted to streak during the mastication of said product.

17. A chewable product as in claim 15 in which said colorant is adapted to provide a speckled appearance during the mastication of said product.

18. A chewable product as in claim 16 which is bubble gum.

19. A chewable product as in claim 17 which is bubble gum.

20. A chewable product as in claim 12 in which said active ingredient comprises as least one flavorant.

21. A chewable product as in claim 12 in which said active ingredient comprises at least one effervescent agent.

22. A chewable product as in claim 21 in which said effervescent agent is adapted to generate $CO_2$ during the mastication of said product.

23. A chewable product as in claim 12 in which said active ingredient comprises tobacco.

24. A chewable product as in claim 12 in which said active ingredient comprises as least one medicament.

25. A chewable product as in claim 9 in which a plurality of said active ingredients are employed therein.

26. A chewable product as in claim 25 in which said plurality of active ingredients comprise two or more of intense sweetener, colorant, flavorant, medicament, tobacco and effervescent agent.

27. A chewable product as in claim 11 which is bubble gum.

28. A chewable product as in claim 11 which is regular chewing gum.

29. A chewable product as in claim 6 in which said active ingredient is selected from the group consisting of flavorants, intense sweeteners, colorants, medicaments, effervescent agents and tobacco.

30. A chewable product as in claim 29 in which said active ingredient is an intense sweetener.

31. A chewable product as in claim 30 in which said active ingredient is aspartame.

32. A chewable product as in claim 30 in which said active ingredient is acid saccharin or a salt thereof.

33. A process for extending the release time of an active ingredient in a chewable product which comprises physically encapsulating at least one of said active ingredients in particles of water-insoluble elastomer selected from the group consisting of polyisobutylene, butyl rubber, styrene butadiene rubber, chicle, crown gum, nispero, balato, jetulong, pendare, perillo, niger, gutta, tunic, leche caspi, sorva, and gutta hand kang prior to the formulating of said active ingredient into, and the masticating of said active ingredient from, said chewable product, whereby the rate of release of said active ingredient from said chewable product is retarded due to the need to first masticate said active ingredient from said elastomer particles, said elastomer particles having a size of about 100 to 1200 microns and said active ingredient being in the form of a liquid or a solid and when in solid form having a particle size less than that of said solid particles of elastomer and being about 10 to 1000 microns.

34. In a process for encapsulating at least one active ingredient for a chewable product so as to extend the release time of said active ingredient from said chewable product the improvement comprising physically encapsulating said active ingredient in non-porous, chewable, particles of a food grade water-insoluble elastomer selected from the group consisting of polyisobutylene, butyl rubber, styrene butadiene rubber, chicle, crown gum, nispero, balato, jetulong, pendare, perillo, niger, gutta, tunic, leche caspi, sorva, and gutta hand kang and then incorporating the encapsulated active ingredient in said chewable product, said particles of elastomer having a particle size of about 200 to 1200 microns and said active ingredient being in the form of a liquid or a solid and when in solid form having a particle size less than that of said solid particles of elastomer and being about 10 to 1000 microns.

35. A chewable product designed for canine or feline use and comprising a plurality of non-porous, chewable, particles of a water-insoluble elastomer encased active ingredient, said solid particles of elastomer having a particle size of about 200 to 1200 microns and comprising an elastomer selected from the group consisting of polyisobutylene, butyl rubber, styrene butadiene rubber, chicle, crown gum, nispero, balato, jetulong, pendare, perillo, niger, gutta, tunic, leche caspi, sorva, and gutta hand kang and said active ingredient being in the form of a liquid or a solid and when in solid form having a particle size less than that of said solid particles of elastomer and being about 10 to 1000 microns, said active ingredients being encapsulated in said solid particle of elastomer so as to facilitate the release of said active ingredient over a prolonged period of time when said product is chewed.

36. A process for physically encapsulating at least one active ingredient for chewable products selected from the group consisting of flavorants, sweeteners, colorants, medicaments, tobacco and effervescent agents which comprises
admixing said active ingredient with a continuous phase of elastomer to form a homogeneous dispersion of said active ingredient in said elastomer,
cooling said homogeneous dispersion to below the brittle point thereof, and
pulverizing the embrittled dispersion to form non-porous particles thereof having an average particle size of about 200 to 1200 $\mu$m.

37. A chewing tobacco product comprising a plurality of non-porous, chewable, particles of a water-insoluble elastomer based composition encased active ingredient, said solid particles of elastomer based composition having a particle size of about 200 to 1200 microns and said active ingredient being in the form of a liquid or a solid and when in solid form having a particle size less than that of said solid particles of elastomer based composition and being about 10 to 1000 microns, said active ingredients being encapsulated in said solid particles of elastomer based composition so as to facilitate the release of said active ingredient over a prolonged period of time when said product is chewed.

38. A chewable bolus comprising a plurality of non-porous, chewable, particles of a water-insoluble elastomer based composition encased active ingredient, said solid particles of elastomer based composition having a particle size of about 200 to 1200 microns and said active ingredient being in the form of a liquid or a solid and when in solid form having a particle size less than that of said solid particles of elastomer based composition and being about 10 to 1000 microns, said active ingredients being encapsulated in said solid particles of elastomer based composition so as to facilitate the release of said active ingredient over a prolonged period of time when said product is chewed.

39. A chewable non-consumable baby product comprising a plurality of non-porous, chewable, particles of a water-insoluble elastomer based composition encased active ingredient, said solid particles of elastomer based composition having a particle size of about 200 to 1200 microns and said active ingredient being in the form of a liquid or a solid and when in solid form having a particle size less than that of said solid particles of elastomer based composition and being about 10 to 1000 microns, said active ingredients being encapsulated in said solid particles of elastomer based composition so as to facilitate the release of said active ingredient over a prolonged period of time when said product is chewed.

40. An athletic mouthpiece comprising a plurality of non-porous, chewable, particles of a water-insoluble elastomer based composition encased active ingredient, said solid particles of elastomer based composition having a particle size of about 200 to 1200 microns and said active ingredient being in the form of a liquid or a solid and when in solid form having a particle size less than that of said solid particles of elastomer based composition and being about 10 to 1000 microns, said active ingredients being encapsulated in said solid particles of elastomer based composition so as to facilitate the release of said active ingredient over a prolonged period of time when said product is chewed.

41. An animal bit comprising a plurality of non-porous, chewable, particles of a water-insoluble elastomer based composition encased active ingredient, said solid particles of elastomer based composition having a particle size of about 200 to 1200 microns and said active ingredient being in the form of a liquid or a solid and when in solid form having a particle size less than that of said solid particles of elastomer based composition and being about 10 to 1000 microns, said active ingredients being encapsulated in said solid particles of elastomer based composition so as to facilitate the release of said active ingredient over a prolonged period of time when said product is chewed.

42. A process for physically encapsulating at least one additive in a water-insoluble elastomeric matrix which comprises
   admixing said additive with a continuous water-insoluble phase of elastomer to form a homogeneous dispersion of said additive in said elastomer,
   cooling said homogeneous dispersion to below the brittle point thereof, and
   pulverizing the embrittled dispersion to form nonporous particles thereof having an average particle size of about 200 to 1200 μm.

43. A process as in claim 42 in which said additive is a food grade material.

44. A process as in claim 43 in which said elastomer is a food grade material.

* * * * *